United States Patent [19]

Meade

[11] Patent Number: 4,988,731
[45] Date of Patent: Jan. 29, 1991

[54] SODIUM HYDROGEN DIVALPROATE OLIGOMER

[75] Inventor: Edwin M. Meade, Duncan, Canada

[73] Assignee: Abbott Laboratories, Abbott Park, Ill.

[21] Appl. No.: 117,945

[22] Filed: Nov. 9, 1987

Related U.S. Application Data

[63] Continuation-in-part of Ser. No. 68,284, Aug. 20, 1979, abandoned.

[51] Int. Cl.$^5$ ..................... A61K 31/00; C07C 53/128
[52] U.S. Cl. .................... 514/557; 562/606
[58] Field of Search ........................ 562/606; 514/557

[56] References Cited

U.S. PATENT DOCUMENTS

| | | | |
|---|---|---|---|
| 2,895,976 | 7/1959 | Kairys et al. | 260/419 |
| 2,915,537 | 12/1959 | Meade | 260/419 |
| 4,127,604 | 11/1978 | Chignac et al. | 562/606 |
| 4,558,070 | 12/1985 | Bauer et al. | 514/557 |

FOREIGN PATENT DOCUMENTS

| | | | |
|---|---|---|---|
| 1074978 | 10/1954 | France | 562/606 |
| 2442M | 4/1964 | France | 562/606 |

OTHER PUBLICATIONS

"The Pharmacological Studies on Sodium Dipropylacetate Anticonvulsant Activities and General Pharmalogical Actions", K. Shuto and T. Nishigaki, Applied Pharmacology, 4[6], pp. 937–949 (1970).

*Primary Examiner*—Vivian Garner
*Attorney, Agent, or Firm*—Steven F. Weinstock

[57] ABSTRACT

This invention concerns certain diethyl- or dipropylacetic acid salts of sodium valproate which have physiological properties similar to those of valproic acid or sodium valproate but show highly superior stability characteristics.

2 Claims, No Drawings

SODIUM HYDROGEN DIVALPROATE OLIGOMER

This is a continuation-in-part of copending application Serial No. 68,284, filed Aug. 20, 1979 now abandoned.

This invention relates to salts of valproic acid. In the last decade, 2-propylpentanoic acid and its alkali or earth alkali salts (hereinafter referred to as valproic acid and valproates or valproate salts, respectively) have been introduced in the arsenal of drugs useful for treating epileptic seizures or convulsions. Most commonly used are valproic acid itself or its sodium salt. The former is a liquid and as such is less desirable for preparing an oral dosage form while the latter is a solid that has poor stability characteristics partially due to pronounced hygroscopicity.

It has now been found that a highly stable, nonhygroscopic, solid entity can be prepared from valproic acid and its salts, representing a single chemical molecule with welldefined physical characteristics.

The new compound represents a single crystalline entity consisting of one molecule each of valproic acid or diethylacetic and a sodium valproate salt. There has been some uncertainty as to the structure of the compound. It was first hypothesized that the compound formed a complex in the form of a compound thus:

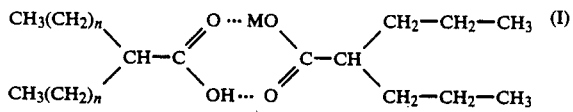

where M represented Na and n is 1 or 2.

Subsequent investigations have confirmed that the compound consists of one molecule each of valproic acid or diethylacetic acid and sodium valproate. However, it has been found that the molecules are distributed as an ionic oligomer, rather than as a dimer as originally believed. Thus, the sodium salt may be illustrated:

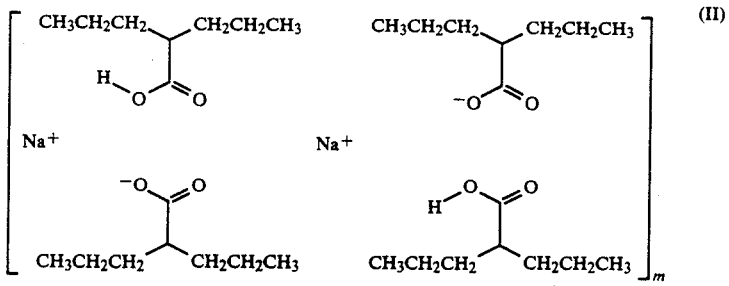

wherein m is about 2.

As can be seen from the foregoing structure, one mole each of the valproic acid moieties form coordinate bonds with the sodium of the sodium valproate molecule, and the valproate ion is ionically bonded to the sodium atom. The structure is thus consistent with the unique characteristics of the compound.

In the simplest embodiment, the above compound is prepared by dissolving one mole each of [Me(CH$_2$)$_n$-]$_2$—CHCOOH and sodium valproate in 1000 ml of acetone at about 50° C. After cooling the solution to 0° C. or below, the formed new compound is filtered, washed if desired with pre-cooled acetone, and dried under reduced pressure to remove all traces of acetone. Alternately, the new compound wherein n=2 can be made in a two-component liquid medium which includes acetone. In this instance, sodium valproate is formed in situ by adding NaOH at a level of one half of a molecular equivalent of the valproic acid present, preferably as a solution in an acetone-miscible solvent for said NaOH, e.q. water. The new compound can be recovered from the liquid phase by evaporating the solvent(s) and, if desired, the new compound can be recrystallized, for instance from acetone/water, from acetonitrile or others, or the material may be spray-dried, lyophilized or purified by chromatography.

The new compound represents a single chemical molecule as can be determined by microanalysis, nmr spectrum, mixed melting point determination, IR spectrum and/or X-ray diffraction. The new compound does not have the aforementioned detrimental physical characteristics of either of the two starting materials; it is a crystalline, stable solid. Surprisingly, such a useful compound can be made only from valproic acid and diethylacetic acid on one side of the molecule, with the sodium or salt of valproic acid. When other valproate salts are used, i.e., the potassium, ammonium or magnesium salts, the resulting compound, either does not crystallize, does not form or is highly unstable in the presence of any atmospheric moisture.

The process for making the compounds of this invention are best illustrated by reference to the following examples which, however, are not intended to limit the invention in any respect.

EXAMPLE 1

In 1000 ml of acetone at about 50° C. is dissolved 166 g of sodium valproate and 144 g of valproic acid. The solution is cooled to about 0° C., filtered and the crystalline precipitate is washed with pre-cooled acetone at about 0° C. The new compound is obtained in a yield of 90% of theory. Additional material can be obtained by using the acetone filtrate in a subsequent batch.

The new material is a stable, white, crystalline powder which melts at 98–100° C. Its moisture stability is established by placing samples of the material for 45 minutes in a controlled environment at room temperature and 80% relative humidity. No weight gain is observed, while under the same condition, the simple sodium salt of valproic acid gains between 17 and 24% in weight.

The infrared spectrum is consistent with proposed structure II and has the following characterizing absorption bands: strong bands at 2957, 2872, 2932, 1685, 1555 and 1370 cm$^{-1}$. The first two of these indicate the various methyl groups, the last two are due respectively to the antisymmetric and symmetric O—C—O—stretching vibrations of the carboxyl salt. The remaining strong bands indicate the stretching vibrations of the various methylene groups and the C=O in the carboxylic acid group, while the weak, broad bands at 2450 and 1900 cm$^{-1}$ are due to intramolecularly bounded OH groups of the carboxylic acid.

EXAMPLE 2

In the fashion of Example 1 but using sodium valproate with the molar equivalents of dibutylacetic acid or diethylacetic acid, respectively, the corresponding hydrogen sodium mixed salts of the assumed structure II with n=b 3 or 1, respectively, are obtained. In the instance of dibutylacetic acid, a very hygroscopic product is obtained which is very difficult to handle and therefore unsuitable for pharmaceutical dosage forms. The mixed salt obtained with diethylacetic acid is a white crystalline powder which is stable to ordinary storage conditions and essentially nonhygroscopic.

EXAMPLE 3

In a comparison of anticonvulsant activities of
A: valproic acid (stable, liquid)
B: sodium valproate (hygroscopic solid)
C: compound (stable solid) of Example 1
the oral ED50 based on equimolar valproic acid equivalents are established by standard procedures. The results are as follows:

|  | A | B | C |
|---|---|---|---|
| Audiogenic seizures (mice) | 154 | 141 | 81 mg/kg |
| Pentylenetetrazole seizures (mice) | <800 | 282 | 178 mg/kg |
| Pentylenetetrazole seizures (rats) | 355 | 415 | 362 mg/kg |

In a bioavailability study carried out with (A) and (C) above in various animal species, the peak blood plasma levels of oral, equimolar doses are determined according to standard procedures, 30 minutes after drug administration.

|  | A | C |
|---|---|---|
| Mouse (200 mg/kg) | 133.7 | 207.4 mg/kg |
| Rat (200 mg/kg) | 84.1 | 63.0 mg/kg |
| Dog (25 mg/kg) | 65.2 | 73.6 mg/kg |
| Dog (25 mg/kg) AUC* | 82.3 | 95.0 hr · mcg/ml |

*Area under the curve value for 0–7 hours.

From the above examples, it will be seen that the new material has equal or better physiological properties than either valproic acid or sodium valproate. Since the new compound has far superior physical characteristics than either "monomer" from which it is made, it greatly facilitates the preparation of solid pharmaceutical dosage forms, and specific amounts can be weighed out and blended with starch and/or other binders to form a flowable powder which can be forwarded to standard tableting machines after granulation. Neither the hygroscopic sodium salt of valproic acid nor the liquid valproic acid itself can be processed in this fashion without special precautions or absorbents.

The new compounds can be tableted in accordance with Example XIII of U.S. Pat. No. 3,325,361 and analogous methods. In these procedures, one or more diluents and/or excipients are used, e.g., starch, talcum powder, lubricants, disintegrators, flavoring agents, coloring agents and the like. These additives, of course, are the usual pharmaceutically acceptable carriers or diluents employed in routine fashion by tablet formulators.

The above structure II is the most likely true two-dimensional view of the sodium/hydrogen divalproate and seems to be confirmed by IR and nmr spectra, by molecular weight and microanalytic values. Thus, the new material should be characterized not by depicting a structural formula but by reference to a single compound of formula $(CH_3CH_2CH_2)_2CHCO_2Na/R_2CHCO_2H$ or $[(R_2CHCO_2)(R_2CHCO_2)]Na,H$ wherein each R is propyl, or by reference to sodium/hydrogen divalproate.

It will be understood that various changes and modifications can be made in the details of procedure, formulation and use without departing from the spirit of the invention, especially as defined in the following claims.

I claim:

1. An oligomer having a 1:1 molar ratio of sodium valproate and valproic acid of the unit formula, $(CH_3CH_2CH_2)_2CHCO_2Na/(CH_3CH_2CH_2)_2CHCO_2H$, and containing about 4 such units.

2. An oral pharmaceutical dosage form for treating the symptoms of epileptic seizures or convulsions, containing as the active principal an oligomer having a 1:1 molar ratio of sodium valproate and valproic acid of the unit formula, $(CH_3CH_2CH_2)_2CHCO_2Na/(CH_3CH_2CH_2)_2CHCO_2H$, and containing about 4 such units.

* * * * *